United States Patent
Ferentini et al.

(10) Patent No.: US 11,406,534 B2
(45) Date of Patent: Aug. 9, 2022

(54) DRAINAGE DEVICES AND METHODS FOR DRAINING THE AQUEOUS HUMOR OF THE EYEBALL

(71) Applicants: Gabriele Ubaldo Ferentini, Milan (IT); Fabio Ferentini, Magenta (IT)

(72) Inventors: Gabriele Ubaldo Ferentini, Milan (IT); Fabio Ferentini, Magenta (IT)

(*) Notice: Subject to any disclaimer, the term of this patent is extended or adjusted under 35 U.S.C. 154(b) by 676 days.

(21) Appl. No.: 16/335,687

(22) PCT Filed: Sep. 28, 2017

(86) PCT No.: PCT/IB2017/055951
§ 371 (c)(1),
(2) Date: Mar. 22, 2019

(87) PCT Pub. No.: WO2018/060912
PCT Pub. Date: Apr. 5, 2018

(65) Prior Publication Data
US 2019/0388273 A1  Dec. 26, 2019

(30) Foreign Application Priority Data
Sep. 30, 2016 (IT) .................. 102016000098246

(51) Int. Cl.
*A61F 9/007* (2006.01)

(52) U.S. Cl.
CPC .. *A61F 9/00781* (2013.01); *A61F 2220/0008* (2013.01); *A61F 2230/0019* (2013.01)

(58) Field of Classification Search
CPC .......... A61F 9/00781; A61F 2220/0008; A61F 2230/0019; A61F 9/0017; A61M 27/002
See application file for complete search history.

(56) References Cited

U.S. PATENT DOCUMENTS

| | | | |
|---|---|---|---|
| 5,454,796 A * | 10/1995 | Krupin | A61F 9/00781 604/9 |
| 5,476,445 A | 12/1995 | Baerveldt et al. | |
| 5,752,928 A * | 5/1998 | de Roulhac | A61F 9/00781 604/9 |
| 6,589,203 B1 * | 7/2003 | Mitrev | A61F 9/00781 604/27 |
| 2005/0267398 A1 * | 12/2005 | Protopsaltis | A61F 9/00781 604/8 |
| 2010/0241046 A1 * | 9/2010 | Pinchuk | A61L 31/146 604/8 |
| 2013/0150773 A1 | 6/2013 | Nissan et al. | |
| 2016/0058616 A1 * | 3/2016 | Camras | A61F 9/00781 604/9 |

\* cited by examiner

*Primary Examiner* — Nicholas J. Weiss
*Assistant Examiner* — Alessandro R Del Priore
(74) *Attorney, Agent, or Firm* — ArentFox Schiff LLP; Michael Fainberg

(57) ABSTRACT

Drainage devices are provided for draining aqueous humor present in the anterior chamber of an eyeball. Such devices include a drainage tube extending axially along a tube axis between a distal end and a proximal end. The distal and proximal ends are at least partially open and are beveled in the same direction. A support flange extends from the proximal end of the drainage tube and includes a plate-shaped portion having an upper surface and a lower surface. The proximal end of the drainage tube is sloped so as to make its opening face the upper surface of the plate-shaped portion. Methods for draining aqueous humor present in the anterior chamber of an eye are also provided.

10 Claims, 4 Drawing Sheets

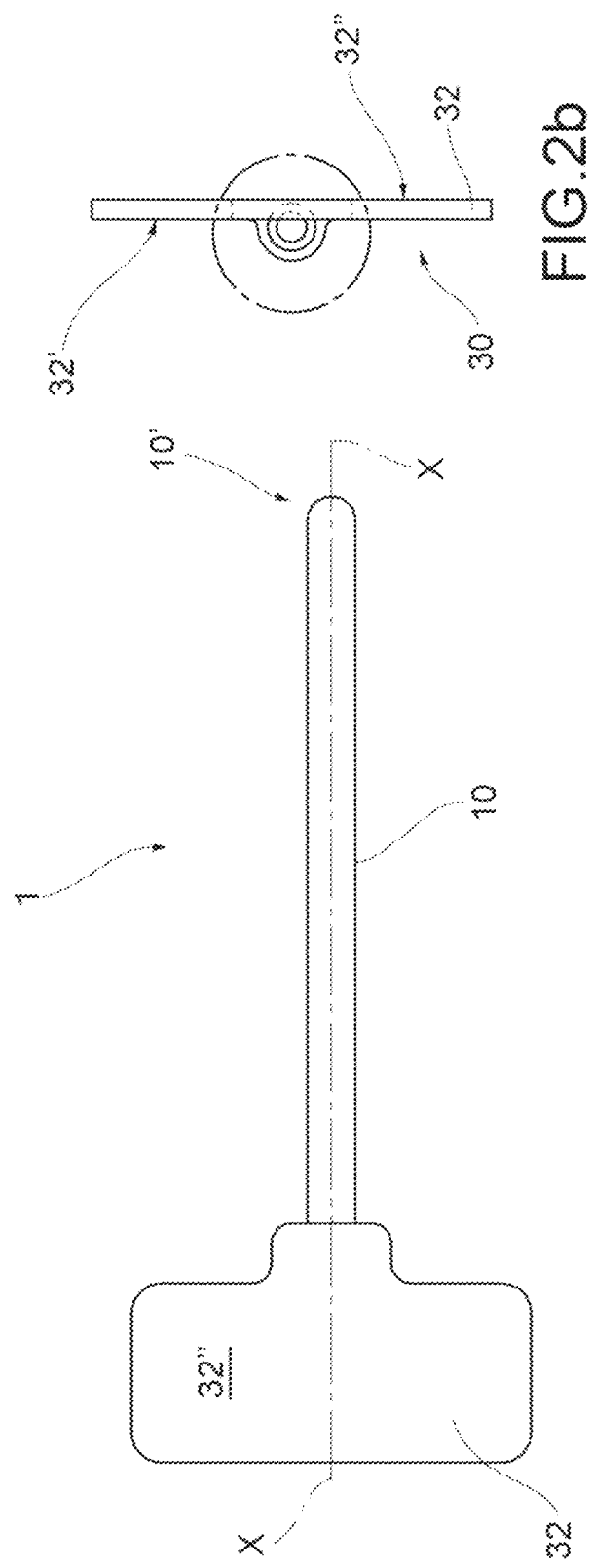
FIG.2
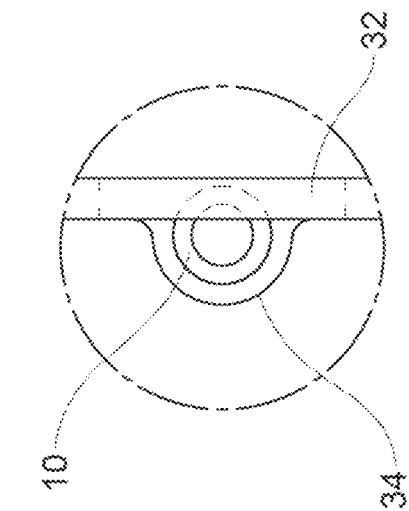
FIG.3
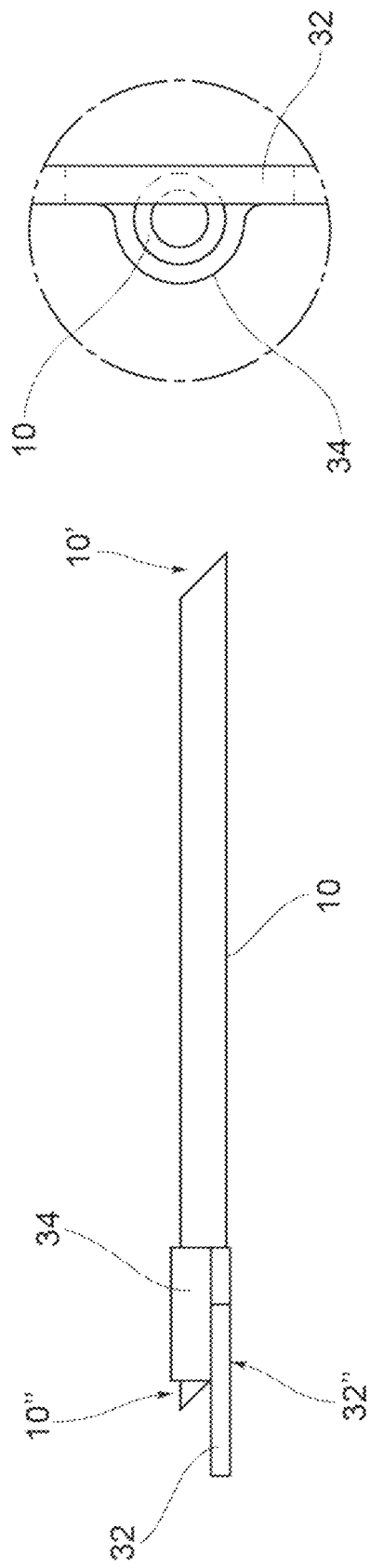
FIG.2a
FIG.2b

DRAINAGE DEVICES AND METHODS FOR DRAINING THE AQUEOUS HUMOR OF THE EYEBALL

CROSS-REFERENCE TO RELATED APPLICATIONS

This application is a National Phase Application of PCT International Application No. PCT/IB2017/055951, International Filing Date, Sep. 28, 2017, claiming priority to Italian Patent Application No. 102016000098246, filed Sep. 30, 2016, each of which is hereby incorporated by reference in its entirety.

FIELD OF THE INVENTION

The present invention relates to the field of ophthalmic surgery and in particular techniques for the treatment of glaucoma.

The object of the invention is a device and a method for draining the aqueous humor present in the anterior chamber of the eyeball. This device, also known in the technical jargon as a "shunt", is used to reduce intraocular pressure, one of the major causes of the onset of glaucoma.

BACKGROUND OF THE INVENTION

The term "glaucoma" covers a series of ocular pathological conditions characterized by anatomical changes in the optic nerve head, impairment of the visual field, and an increase in intraocular pressure.

In this heterogeneous group of pathologies, the most well-known, and one of the major causes of blindness worldwide, is Primary Open Angle Glaucoma (POAG). It is a slowly progressive, chronic optic neuropathy with spontaneous progression toward blindness if not treated, and generally bilateral (though its severity may be asymmetric between the two eyes).

In effect, there is a progressive loss of retinal ganglion cells and nerve fibers in the optic nerve, and since these fibers gather luminous stimuli from certain areas of the retina, the afflicted patient progressively loses actual "zones" of his/her field of vision, until the advanced stages of the disease result in first tunnel vision and ultimately total blindness.

The known risk factors for possible development of glaucomatous damage of the optic nerve are many: one of the most important is elevated intraocular pressure. Other risk factors are: myopia, changes in the appearance of the optic nerve and the retinal nerve fiber layer, advanced age, family history, black race, diabetes mellitus and cardiovascular disease.

The etiopathogenetic mechanisms through which glaucomatous pathology causes damage to the nerve fibers of the optic nerve are, on the one hand, the compression exerted by the increased interocular pressure on nerve fibers with direct mechanical action, and, on the other, vascular factors (such as a vascular perfusion deficiency when the diastolic pressure drops below critical values for protracted periods inducing ischemia in the nerve).

Currently, the only way to treat glaucoma is to reduce intraocular pressure when it exceeds normal values for long periods. The eye constantly produces a liquid similar to water called aqueous humor; the production site is the ciliary processes and from there the aqueous humor fills the posterior chamber, i.e. the space between the crystalline lens and the back of the iris, and then flows into the anterior chamber, or the space between the iris and the cornea. The aqueous humor must exit the anterior chamber through a complex structure called the "trabecular meshwork", which may be compared to a filter, and then is immersed in an adjacent tubular structure called the "Schlemm's canal", flows into the aqueous veins and then into the venous plexus.

The ocular pressure increases when the balance between the production of aqueous humor and the outflow of the aqueous humor is altered. The anatomical structure that exerts the greatest resistance to the outflow is the trabecular meshwork and the Schlemm's canal. Leaving the eye untreated at high pressure values causes irreversible damage to the ganglionic cells, the retinal nerve fibers and the optic nerve head, which causes permanent and progressive vision loss.

Once a disease diagnosis is made, the therapeutic options are as follows.

Medical therapy with hypotonic drops.

These drops work by reducing the intraocular pressure; in particular, they either reduce the production of aqueous humor or increase its absorption or facilitate outflow. The most commonly used class of drugs are beta blockers, topical carbon dioxide antagonists, alpha 2 selective agonists, prostaglandins and prostamides and parasympathomimetics.

Usually one chooses to start with a monotherapy and, if the ocular pressure cannot be brought down to normal values, more drops in combination may be added. Among other treatments, preparations are available containing fixed combinations of two ingredients that are useful for improving compliance with the prescribed therapy.

Laser Therapy.

Parasurgical therapies may be used, such as ALT (argon laser trabeculoplasty, no longer in use) or SLT (selective laser trabeculoplasty), which, through the use of a laser, seek to increase the outflow of the aqueous humor at the trabecular level. The former therapy has a thermal action mechanism and creates holes in the trabecular meshwork; the latter therapy has a biological action to stimulate the production of cytokine.

Surgery.

Surgical therapy for glaucoma has been traditionally prescribed when medical or laser therapy is ineffective or when there is a doubt that the drops are being properly used by the patient.

However, in the last decade, surgery has also been proposed as a first therapeutic choice, based on better and more stable pressure control, a reduction in periodic visits and, ultimately, a reduced impact on the quality of life of the patient.

In all cases, surgical therapy should be seriously considered when the glaucoma is not sufficiently controlled and manifests progressive documented damage or high risk of the disease's progression.

Surgical therapy for glaucoma employs numerous techniques that are all aimed at reducing eye pressure by reducing resistance to the outflow of the aqueous humor by creating an artificial passage for the same.

The main types of procedures are trabeculectomy, non-penetrating interventions (such as deep sclerotomy and viscocanalostomy), and drainage implants.

Trabeulectomy has been the most common procedure since 1969. It consists of detaching the capsule and the conjunctiva and creating a scleral flap in the underlying space, removing a portion of the trabecular meshwork, performing an iridectomy, i.e. removing a part of the iris, and suturing the scleral flap and the conjunctiva. In this way, the aqueous humor can flow from the inside of the eye outward, i.e. in the sub-conjunctival space without passing through the resistance of the trabecular meshwork and the Schlemm's canal.

Drainage systems have had a remarkable development over the last two decades. These are compound outflow systems, in most cases, using a tube that communicates with a collection reservoir placed outside the sclera and diffusing the aqueous humor under the Tenon's capsule and the conjunctiva. The tube is inserted into the anterior chamber and drains the aqueous humor posteriorly toward the reservoir without passing through the trabecular meshwork.

The drainage area that is created is thus sufficiently wide and posteriorly positioned so as to be less affected by the cicatricial processes of the conjunctiva and the Tenon's capsule that would cause the procedure to fail.

The cicatricial processes are in fact the most significant cause of failure of any type of glaucoma procedure. Usually, the reservoir has a cross-section greater than 1 $cm^2$ and the tube has a length of more than 15 mm.

Among the most frequently used drainage implants are the Baerveldt and Molteno valves, and the Ahmed and Krupin implants. These implants are considered when classic trabeculectomy procedures do not yield the desired results.

The results of drainage implants available today are quite variable in relation to the base pathology. Generally, an ocular tension of less than 21 mmHg with or without adjuvant therapy is obtained in about 53-74% of cases at 2 years from the procedure. However, drainage implants have many of the typical complications of fistulizing procedures. Moreover, they are characterized by a first post-operative period wherein hypertonicity or hypotonicity is possible. In some cases, a diplopia is possible secondary to an impediment of ocular motility due to the valve plate. In the long term, a gradual rise in tonicity or a failure of the procedure is possible.

Most recently conceived drainage devices are much simpler than the aforesaid devices, as they are composed of a microtube provided with appendages for stabilization or with an angle of curvature for positioning. In all cases, they make the surgical procedure simpler than the trabeculectomy. Their design is made to drain the aqueous humor into the sub-conjunctival space or Schlemm's canal or in the suprachoroidal space.

Implant techniques are defined as ab externo when the drainage device is inserted from the outside of the sclera to the inside of the eye, and more precisely, in the anterior chamber. They are defined as ab interno when the device is introduced from the anterior chamber outward without detaching the conjunctiva. In all cases, the procedure is simpler than the trabeculectomy.

SUMMARY OF THE INVENTION

The object of the present invention is to provide a drainage device that will make the surgical procedure even more effective, faster and less stressful for the patient and surgeon.

Such objects are achieved with drainage devices and drainage methods as described herein. Further features and advantages of the devices and the drainage methods according to the invention will become evident from the description of representative embodiments, provided by way of non-limiting examples, with reference to the attached drawings.--

BRIEF DESCRIPTION OF THE FIGURES

FIGS. 2, 2a, 2b are plan, side and end views of the drainage device, respectively;

FIG. 3 is an enlarged view of the detail circled in FIG. 2b; and

DETAILED DESCRIPTION

Figure 1:
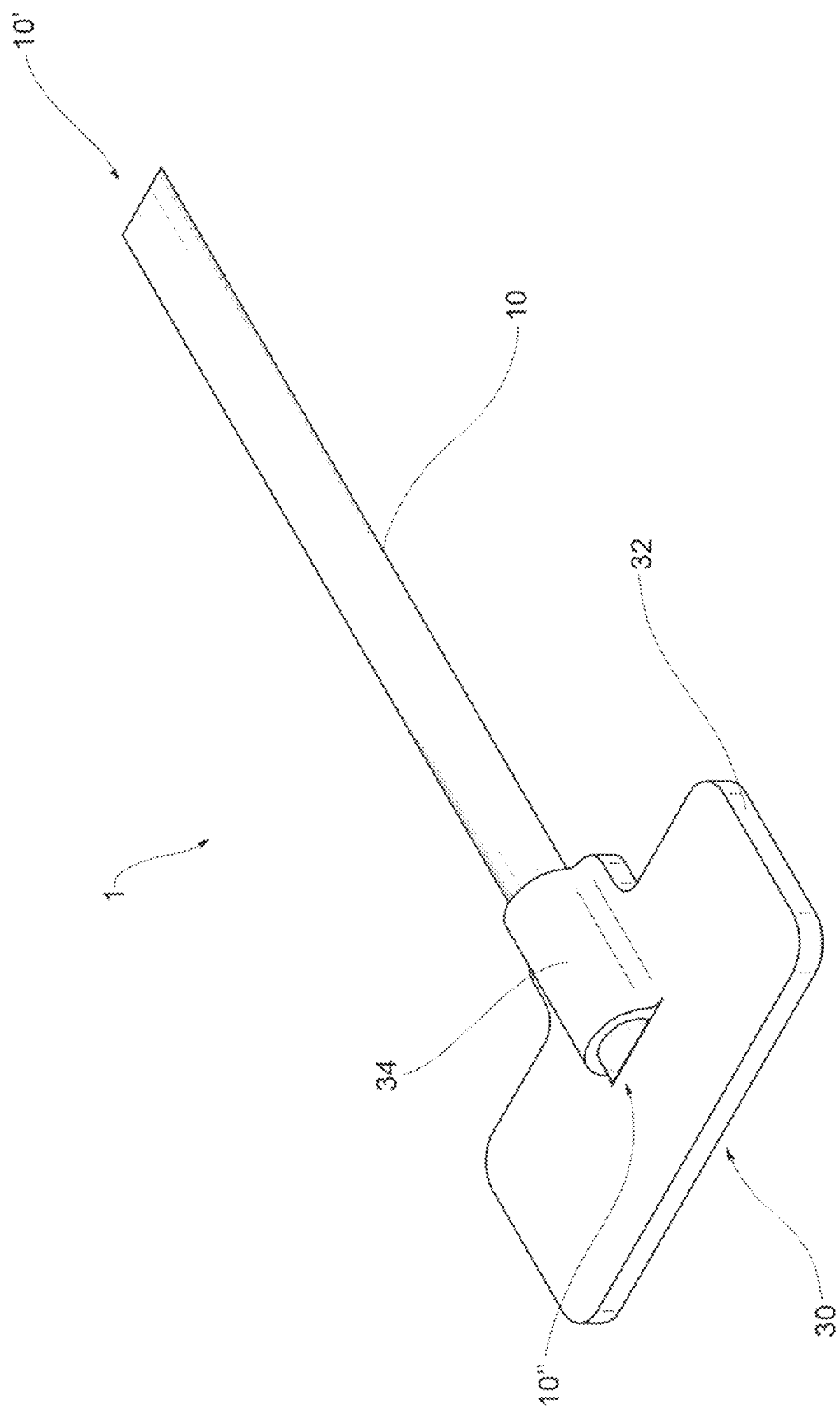
FIG. 1 is a perspective view of the drainage device according to the invention.
Figure 1A:
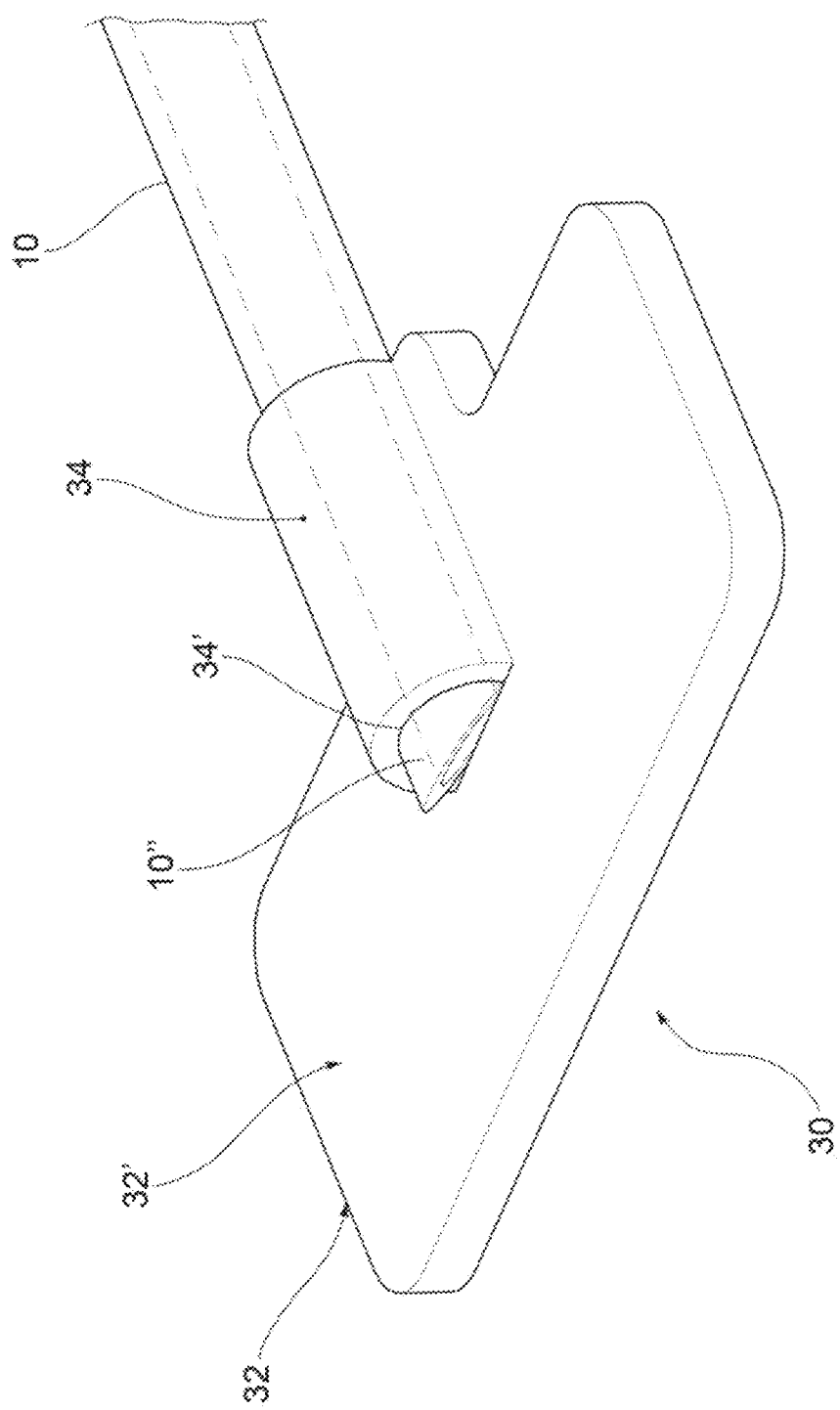
FIG. 1a is an enlarged view of a proximal portion of the device.

In said drawings, a drainage device for draining the aqueous humor present in the anterior chamber of the eyeball is indicated collectively at 1.

In a general embodiment, the drainage device 1 comprises a drainage tube 10 and a support flange 30.

The drainage tube 10 extends axially along a tube axis X between a distal end 10' and a proximal end 10". The distal 10' and proximal 10" ends are at least partially open and are beveled in the same direction. For example, the slope of the ends is between 30° and 60° with respect to the tube axis X, preferably about 45°.

In one embodiment, the distal end 10' is completely open.

In one embodiment, the proximal end 10" is fully open and partially closed by the support flange 30 when the drainage tube 10 is coupled to the support flange 30, as will be described below.

The support flange 30 extends from the proximal end 10" of the drainage tube 10 and comprises a plate-shaped portion 32 which extends both in an axial direction and in an orthogonal direction with respect to the tube axis X. In a preferred embodiment, the plate-shaped portion 32 extends predominantly in an orthogonal direction with respect to the tube axis X.

This plate-shaped portion 32 is delimited by an upper surface 32' and a lower surface 32".

In one embodiment, the upper 32' and lower 32" surfaces are flat surfaces.

The proximal end 10" of the drainage tube 10 is sloped so as to make its opening face the upper surface 32' of the plate-shaped portion 32. Thus, the fluid entering in the distal end 10' of the drainage tube is directed to this upper surface 32'.

In one embodiment, the support flange 30 extends symmetrically with respect to the tube axis X.

For example, the plate-shaped portion 32 of the support flange 30 has a substantially rectangular shape, with the longer sides perpendicular to the axis of the tube X.

Therefore, in one embodiment, the drainage device 1, seen in plan view (FIG. 2), generally has a "T" shape.

In one embodiment, the proximal end 10" of the drainage tube 1 is axially spaced from the proximal side of the plate-shaped portion 32.

In the illustrated embodiment, the proximal end 10" of the drainage tube 10 is open on a central portion of the upper surface 32' of the plate-shaped portion 32.

In one embodiment, the support flange 30 comprises a tubular portion 34 coupled to the drainage tube 10. A proximal portion of the drainage tube 10 is inserted with a shaped coupling in this tubular portion 34. "Shaped coupling" means that there is substantially no play between the outer side wall of the drainage tube 10 and the inner side wall of the tubular portion 34.

To allow the drainage tube 10 to be open on the upper surface 32' of the plate-shaped portion 32, the tubular portion 34 has a proximal opening 34' at least partially open towards the upper surface 32' of the plate-shaped portion 32.

In one embodiment, the thickness of the plate-shaped portion 32 partially occludes both the open proximal end 10" of the drainage tube 10 and the proximal opening 34' of the tubular portion 34.

In other words, the tubular portion 34 is made partly in the thickness of the plate-shaped portion 32 and partly protrudes from the upper surface 32' thereof. For example, the thickness of the plate-shaped portion 32 is equal to or less than the radius of the tubular portion 34.

Thus, in the illustrated embodiment, the open proximal end 10" of the drainage tube 10 projects beyond the proximal opening 34' of the tubular portion 34 only for the upper portion of the bevel that surpasses in height the thickness of the plate-shaped portion 32.

In one embodiment, the drainage tube 10 and the support flange 30 are substantially coplanar to each other.

In one embodiment, the drainage tube 10 has no openings along its side wall. In other words, the only openings made in the drainage tube 10 are those at its distal and proximal ends.

In one embodiment, the drainage tube 10 and the tubular portion 34 are stably connected to each other, for example by force, or by bonding, or by co-molding.

In one embodiment, the drainage tube 10 is made of a high-performance plastic material, for example polyimide or a similar biocompatible material.

In one embodiment, the drainage tube 10 has a length between 3.5 and 6 mm, preferably about 4.5 mm, an outer diameter between 0.2 and 0.3 mm, and a wall thickness between 0.04 and 0.06 mm.

In one embodiment, the support flange 30 is made of a high performance technopolymer, such as polyetherimide or a similar biocompatible material, preferably for molding or even mechanical machining.

In one embodiment, the support flange has a thickness comprised between 0.1 mm and 0.25 mm and a dimension transverse or orthogonal to the tube axis X between 1.5 mm and 2.5 mm.

Figure 4:
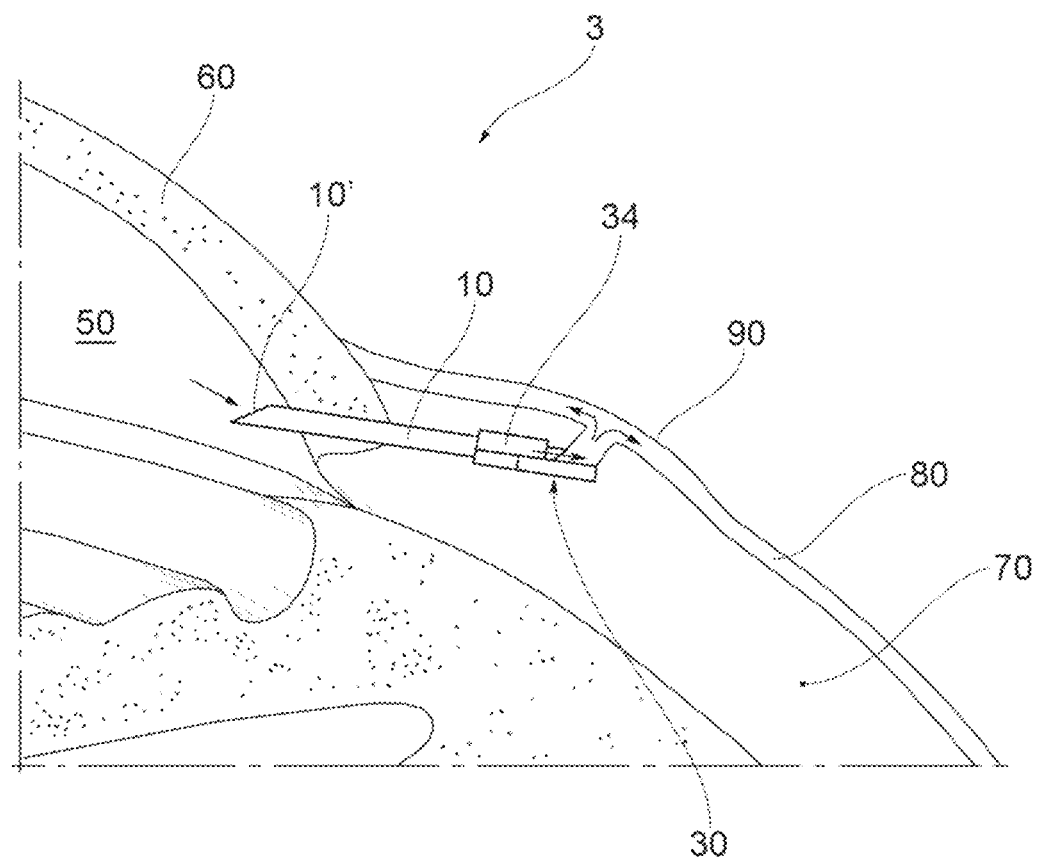
FIGS. 4 and 5 show schematically the drainage device positioned in the eyeball.
Figure 5:
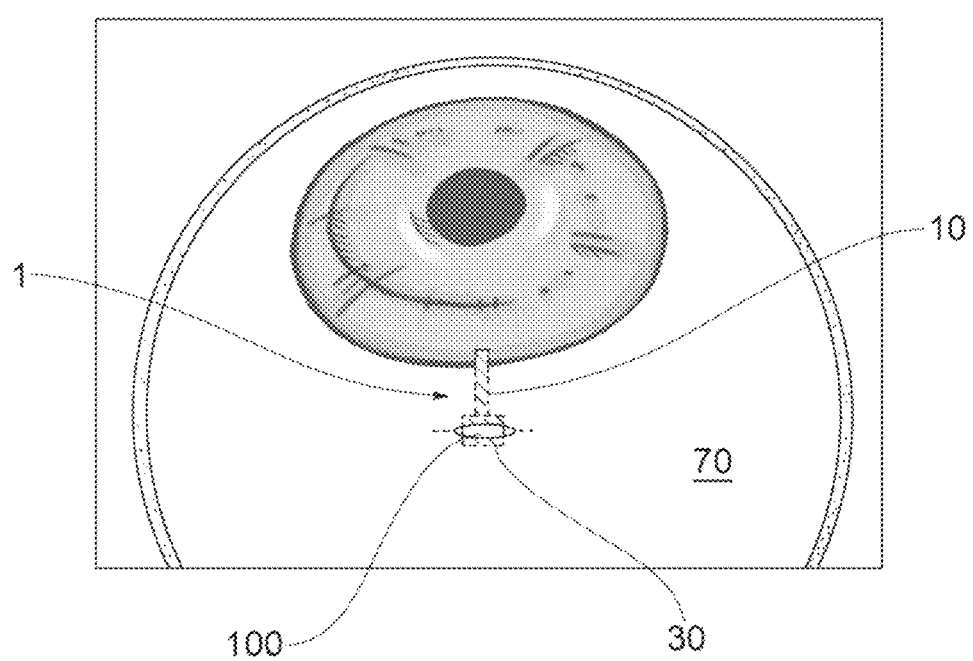

Referring to FIGS. 4 and 5, the invention also relates to a drainage method for draining the aqueous humor in the anterior chamber 50 of the eyeball 3 through the drainage device 1 described above. The drainage device is positioned with the distal end 10' of the drainage hose 10 inside the anterior chamber 50 with the opening of the distal end 10' facing the cornea 60 and with the support flange 30 inside the sclera 70, without contact with the capsule 80 and the conjunctiva 90.

Specifically, the surgical technique for inserting the drainage device 1 is ab externo: the capsule and the conjunctiva must therefore be removed from the sclera, preferably between the two upper quadrants of the eye.

The point where the device is inserted may be between 10 and 2 o'clock on the sclera while avoiding damaging the vessels, the perforation of which would cause bleeding. The scleral surface should be carefully cauterized to prevent bleeding.

It is advisable to remove the capsule for a scleral surface of about 1 cm² to prevent cicatricial adhesion.

In one embodiment, the distance from the limbus where the incision 100 begins (FIG. 5) is 3.5-4 mm.

The incision 100 is linear, parallel to the limbus, e.g. around 2.5 mm long with a depth of about half the scleral thickness. If, for example, a calibrated micro scalpel is available, it may be set to 200-250 µm. The incision edges are undermined so that the distal part of the support flange 30 may be embedded beneath the distal edge of the incision and the proximal part of the support flange 30 beneath the proximal edge of the incision. This position locks the flange, keeping it from moving either toward the inner part or toward the outer part of the eye.

Using, for example, an angled, no. 23 scalpel or a no. 25 or 27 needle, one penetrates into the anterior chamber through the trabecular meshwork until the tip of the instrument is visible over the iris but not in contact with it.

A tunnel is thus created for threading the drainage device 1. The use of the scalpel is preferable because it encounters less forward resistance and allows better manipulation.

The point of entry is preferably at the center of the linear incision.

Once the tunnel has been made, the drainage device 10 may be inserted by holding the distal end 10' of the drainage tube 10 with the opening facing upwards.

The support flange 30 is positioned under the linear incision so as to keep the edges of the incision separated and raised.

Thus, as indicated by the arrows in FIG. 4, the aqueous humor passes from the anterior chamber to the support flange of the drainage device, and then, passing through the scleral incision, flows under the conjunctiva. The liquid raises the conjunctiva and is then reabsorbed by the venous circulation.

Finally, the conjunctiva is returned to the position it had prior to the procedure, together with the capsule if it has not been removed. The conjunctiva and/or the capsule are sutured with small sutures.

With the drainage device described above, particularly miniaturized, the formation of the mobile scleral flap is avoided, that is, the rectangular incision of the sclera of 4×4 or 4×5 mm currently practiced with some drainage devices and in the trabeculectomy according to the known art.

Moreover, it is not necessary to remove the trabecular meshwork with its scleral corneal component, since the drainage tube according to the invention bypasses this structure.

No iridectomy is required.

It is not necessary to make sutures, as there is no flap to be sealed.

In summary, the drainage device according to the invention allows the aqueous humor to exit from the inside of the eye by avoiding the contact of the trabecular meshwork and the Schlemm's canal, which are the areas with the greatest resistance to outflow.

The end of the drainage tube inside the eye, i.e. the one found in the anterior chamber, is cut in a bevel and is directed towards the cornea so as to avoid being easily occluded by the iris.

Both the drainage tube and the support flange remain inside the sclera so as to avoid contact with the capsule and the conjunctiva and to avoid stimulating the proliferation of cicatricial fibroblasts that could reduce or eliminate its effectiveness.

The inclination of the end of the tube facing the support flange causes the aqueous humor to flow against the flange and this distributes the liquid outside the sclera over its whole breadth. Therefore, any cicatricial phenomena must extend a long way, for example 2 mm, in order to prevent the passage of the aqueous humor.

The shape of the flange and its position with respect to the drainage tube prevent the device from moving away from the position where it was implanted. In effect, the device must not move inside the eye in order to avoid contact with the iris, which could close the fluid access hole, and to prevent the external part of the fluid outlet hole from being too far from the scleral incision, and thus increasing the risk of closure. The device must not be moved outward to avoid an extrusion that would prevent the inner part from drawing out the aqueous humor.

The support flange 30 is constructed to be placed under the scleral incision to keep the edges separated and allow the aqueous humor to flow out more easily due to the width of the support flange. Furthermore, the thickness of the tube and flange lift the edges of the incision by keeping them separated to facilitate the outflow, hampering cicatricial processes.

According to an aspect of the invention, the drainage device is formed only by the tube and the flange. In effect, the drainage device remains in the implant position due to the flange remaining locked in the scleral pocket. No further retention elements are therefore required, with the result that the risk of possible contact of inorganic material with the corneal endothelium is reduced.

The assurance of the passage of the aqueous humor to the external scleral surface and the absence of any device on the external scleral surface to stimulate the fibrosis reaction of the capsule and of the conjunctiva represent a more successful possibility for achieving a reduction of ocular tonicity.

A further advantage of the drainage device according to the invention is that the flange, being intra-scleral, has no close contact with the scleral muscles of the eye and therefore cannot cause ocular motility problems.

Due to the use of the proposed drainage device, it is possible to block any bleeding that may occur during the formation of the tunnel in which the drainage tube is to be inserted. In this case, an endocautery is used, which may not be done with ab interno surgery, as it is almost impossible to retrace the same route of the injector, as one must extract the previously inserted tube.

It is to be noted that the drainage tube of the device according to the invention has a smooth external surface and anchoring is provided with the support flange.

The support flange has a plate-shaped structure and is made of a soft material which, unlike metal, does not produce scleral erosion.

It should also be noted that the tube has an internal diameter such as to automatically limit the laminar flow of aqueous humor.

To the embodiments of the drainage devices and methods described above, those skilled in the art may, to satisfy contingent needs, make modifications, adaptations and replacements of some elements with others that are functionally equivalent, while remaining within the scope of the present invention. Each of the features described in connection with particular embodiments may be realised independently of the other embodiments described herein.

The invention claimed is:

1. A drainage device for draining aqueous humor present in the anterior chamber of an eyeball, comprising:
    a drainage tube extending axially along a tube axis (X) between a distal end and a proximal end, said distal and proximal ends being at least partially open and being beveled, the bevels of said distal and proximal ends being in the same direction; and
    a support flange extending from the proximal end of the drainage tube and comprising a plate-shaped portion having an upper surface and a lower surface,
    the proximal end being sloped so as to make its opening face said upper surface of the plate-shaped portion,
    the proximal end of the drainage tube being open on a central portion of the upper surface of the plate-shaped portion,
    the support flange comprising a tubular portion coupling to the drainage tube,
    a proximal portion of the drainage tube being inserted with a shaped coupling in said tubular portion,
    the tubular portion having a proximal opening at least partially open towards the upper surface of the plate-shaped portion, and
    wherein the thickness of the plate-shaped portion partially occludes both the proximal opening of the drainage tube and the proximal opening of the tubular portion.

2. The drainage device of claim 1, wherein the plate-shaped portion extends mainly in a direction orthogonal to the tube axis (X).

3. The drainage device of claim 1, wherein the support flange extends symmetrically with respect to the tube axis (X).

4. The drainage device of claim 1, wherein the plate-shaped portion of the support flange has a substantially rectangular shape, with its longer sides perpendicular to the axis of the tube (X).

5. The drainage device of claim 1, wherein the tubular portion is made partly in the thickness of the plate-shaped portion and partially protrudes from the upper surface thereof.

6. The drainage device of claim 1, wherein the drainage tube and the support flange are substantially coplanar.

7. The drainage device of claim 1, wherein the drainage tube is without openings along its side wall.

8. A drainage method for draining aqueous humor present in the anterior chamber of an eye by means of the drainage device of claim 1, which provides for positioning the drainage device with the distal end inside the anterior chamber facing towards the cornea and with the support flange inside the sclera, without contact with the capsule and conjunctiva.

9. The drainage method of claim 8, comprising the steps of:
    detaching the capsule and conjunctiva from the sclera;
    performing a linear incision of the sclera, with a depth of about half the scleral thickness;
    making a tunnel from the center of the linear incision to the anterior chamber through the trabecular meshwork;
    inserting the drainage device in the tunnel; and
    placing the support flange under the linear incision so as to keep the edges of the incision apart and raised.

10. The method of claim 9, wherein, after having detached the capsule from the sclera, the capsule is removed for a scleral surface of about 1 $cm^2$.

* * * * *